(12) United States Patent
Prema Mohanasundaram et al.

(10) Patent No.: US 11,642,122 B2
(45) Date of Patent: May 9, 2023

(54) SURGICAL SUTURING INSTRUMENTS

(71) Applicant: Covidien LP, Mansfield, MA (US)

(72) Inventors: Suresh Kumar Prema Mohanasundaram, Chennai (IN); AVVLN Srinivasa Murthy Aravalli, Hyderabad (IN); Jitendra Bhargava Srinivas, Hyderabad (IN); Hari Naga Mahesh Kalepu, Hyderabad (IN)

(73) Assignee: COVIDIEN LP, Mansfield, MA (US)

( * ) Notice: Subject to any disclaimer, the term of this patent is extended or adjusted under 35 U.S.C. 154(b) by 159 days.

(21) Appl. No.: 17/145,997

(22) Filed: Jan. 11, 2021

(65) Prior Publication Data

US 2021/0267587 A1     Sep. 2, 2021

Related U.S. Application Data

(60) Provisional application No. 62/983,003, filed on Feb. 28, 2020.

(51) Int. Cl.
*A61B 17/04*     (2006.01)

(52) U.S. Cl.
CPC ...... *A61B 17/0469* (2013.01); *A61B 17/0491* (2013.01)

(58) Field of Classification Search
CPC ............ A61B 17/0469; A61B 17/0491; A61B 2017/0608; A61B 2017/0609; A61B 17/0625; A61B 17/0483; A61B 17/062; A61B 2017/047; A61B 2017/0472
See application file for complete search history.

(56) References Cited

U.S. PATENT DOCUMENTS

| | | | |
|---|---|---|---|
| 4,027,608 A | 6/1977 | Arbuckle | |
| 5,437,681 A | 8/1995 | Meade et al. | |
| 5,674,229 A | 10/1997 | Tovey et al. | |
| 5,707,379 A | 1/1998 | Fleenor et al. | |
| 5,820,631 A | 10/1998 | Nobles | |
| 5,954,733 A | 9/1999 | Yoon | |
| 5,957,937 A * | 9/1999 | Yoon .................. | A61B 18/1445 606/147 |
| 6,126,665 A | 10/2000 | Yoon | |
| 6,454,777 B1 | 9/2002 | Green | |
| 7,033,370 B2 | 4/2006 | Gordon et al. | |
| 7,062,216 B2 | 6/2006 | Nobe et al. | |
| 7,587,166 B2 | 9/2009 | Aono | |
| 7,588,583 B2 | 9/2009 | Hamilton et al. | |
| 7,776,065 B2 * | 8/2010 | Griffiths ................. | A61B 17/29 606/207 |
| 8,292,905 B2 | 10/2012 | Taylor et al. | |
| 8,702,732 B2 | 4/2014 | Woodard, Jr. et al. | |
| 2011/0270280 A1 * | 11/2011 | Saliman ............. | A61B 17/0469 606/145 |

(Continued)

FOREIGN PATENT DOCUMENTS

| | | | |
|---|---|---|---|
| EP | 0552430 A1 | 7/1993 | |
| EP | 3366227 A1 | 8/2018 | |

*Primary Examiner* — Shaun L David
*Assistant Examiner* — Rachael L Geiger
(74) *Attorney, Agent, or Firm* — Carter, DeLuca & Farrell, LLP

(57) ABSTRACT

Side bite surgical suturing instruments or portions thereof for endoscopic, laparoscopic, endoluminal, and/or transluminal suturing facilitate the use of larger needles to get a bigger bite while suturing.

15 Claims, 4 Drawing Sheets

(56) References Cited

U.S. PATENT DOCUMENTS

2012/0165837 A1\* 6/2012 Belman .............. A61B 17/0469
606/144
2013/0267969 A1 10/2013 Martin et al.
2018/0235601 A1\* 8/2018 Malkowski ...... A61B 17/06066

\* cited by examiner

SURGICAL SUTURING INSTRUMENTS

CROSS-REFERENCE TO RELATED APPLICATION

This application claims the benefit of and priority to U.S. Provisional Patent Application Ser. No. 62/983,003, filed Feb. 28, 2020, the disclosure of which is hereby incorporated by reference in its entirety.

INTRODUCTION

One type of surgical stitch is a purse string suture used to close internal and anal structure or to narrow a passage during a Transanal Total Mesorectal Excision ("TaTME"). TaTME is a surgical approach to remove low rectal and ultra-low rectal tumors and preserve anal sphincters to avoid permanent stomas, thereby restoring a patient's quality of life. Formation of a purse string is a key and primary step in TaTME surgery and is often accomplished using a hand-held surgical instrument.

SUMMARY

In accordance with one aspect of the disclosure, an embodiment of a surgical suturing instrument is provided that includes a handle assembly, a shaft extending distally from the handle assembly, a first jaw member coupled to a distal end portion of the shaft, and a second jaw member. The second jaw member includes a proximal end portion coupled to the distal end portion of the shaft and a distal end portion movably coupled to the proximal end portion and configured for detachable connection of a curved needle.

In aspects, the distal end portion of the second jaw member may be movable relative to the proximal end portion between a first position, in which the distal end portion of the second jaw member is parallel with the proximal end portion, and a second position, in which the distal end portion of the second jaw member extends radially outward from the proximal end portion.

In some aspects, the distal end portion of the second jaw member may be pivotable relative to the proximal end portion.

In further aspects, the second jaw member may include a biasing member that resiliently biases the distal end portion of the second jaw member outwardly relative to the proximal end portion.

In other aspects, the surgical suturing instrument may further include an outer tube disposed about the shaft and configured to move between a proximal position and a distal position. In the proximal position, the outer tube may be disposed proximally of the distal end portion of the second jaw member, and in the distal position the outer tube may be disposed over the distal end portion of the second jaw member.

In aspects, the distal end portion of the second jaw member may be resiliently biased outwardly relative to the proximal end portion, such that the distal end portion of the second jaw member is configured to move from a collapsed state to an expanded state relative to the proximal end portion in response to the outer tube moving from the distal position to the proximal position.

In some aspects, the surgical suturing instrument may further include an axially translatable cable having a distal end portion fixed to the distal end portion of the second jaw member. The cable may be configured to move the distal end portion of the second jaw member relative to the proximal end portion.

In other aspects, the first jaw member may include a proximal end portion coupled to the distal end portion of the shaft, and a distal end portion movably coupled to the proximal end portion of the first jaw member. The distal end portion of the first jaw member may be configured for detachable connection of the curved needle.

In further aspects, the first jaw member may be rotatable about a longitudinal axis defined by the shaft.

In aspects, the proximal end portion of the second jaw member may be fixed to the distal end portion of the shaft.

In some aspects, the first and second jaw members may each define a hole configured for detachable receipt of the curved needle, such that the first and second jaw members are configured to transfer the curved needle therebetween upon rotation of the first jaw member about the longitudinal axis of the shaft relative to the second jaw member.

In further aspects, the hole defined in each of the first and second jaw members may be defined at least partially through the distal end portion of each of the first and second jaw members.

In accordance with another aspect of the disclosure, a surgical suturing instrument is provided that includes a shaft defining a longitudinal axis and having a distal end portion, an outer tube disposed about the shaft and configured to move axially relative to the shaft, a first jaw member, and a second jaw member. The first jaw member includes a proximal end portion coupled to the distal end portion of the shaft, and a distal end portion movably coupled to the proximal end portion of the first jaw member and configured for detachable connection of a curved needle. The second jaw member includes a proximal end portion coupled to the distal end portion of the shaft, and a distal end portion movably coupled to the proximal end portion of the second jaw member and configured for detachable connection of the curved needle. The distal end portion of the first jaw member is configured to move relative to the proximal end portion of the first jaw member in response to movement of the outer tube. The distal end portion of the second jaw member is configured to move relative to the proximal end portion of the second jaw member in response to movement of the outer tube.

In aspects, the distal end portion of the first jaw member may be movable relative to the proximal end portion of the first jaw member between a first position and a second position. In the first position, the distal end portion of the first jaw member is coaxial with the proximal end portion of the first jaw member, and in the second second position the distal end portion of the first jaw member is angled outward from the proximal end portion of the first jaw member.

In some aspects, the distal end portion of the first jaw member may be pivotable relative to the proximal end portion of the first jaw member.

In other aspects, the first jaw member may include a biasing member that resiliently biases the distal end portion of the first jaw member outwardly relative to the proximal end portion of the first jaw member.

In further aspects, the outer tube may be configured to move between a proximal position, in which the outer tube is disposed proximally of the distal end portion of each of the first and second jaw members, and a distal position, in which the outer tube is disposed over the distal end portion of each of the first and second jaw members to maintain the first and second jaw members in a collapsed state.

In accordance with yet another aspect of the disclosure, an end effector assembly of a surgical suturing instrument is provided that includes a body portion, a first jaw member coupled to the body portion and configured for detachable connection of a needle, and a second jaw member. The second jaw member includes a proximal end portion coupled to the body portion, and a distal end portion coupled to the proximal end portion and configured to move relative to the proximal end portion between a first position and a second position. In the first position, a longitudinal axis defined by the distal end portion of the second jaw member is disposed at a first angle relative to the proximal end portion, and in the second position the longitudinal axis of the distal end portion of the second jaw member is disposed at a second angle relative to the proximal end portion. The second angle is greater than the first angle. The distal end portion of the second jaw member is configured for detachable connection of the needle.

In aspects, the first angle may be about zero degrees and the second angle may be from about 5 degrees to about 90 degrees.

In other aspects, the distal end portion of the second jaw member may have a distal end. The distal end may be disposed coaxially with a longitudinal axis defined by the proximal end portion when the distal end portion of the second jaw member is in the first position. The distal end may be disposed outside of the longitudinal axis defined by the proximal end portion when the distal end portion of the second jaw member is in the second position.

Further details and aspects of exemplary embodiments of the disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

BRIEF DESCRIPTION OF THE DRAWINGS

The accompanying drawings, which are incorporated in and constitute a part of the specification, illustrate embodiments of the disclosure and, together with a general description of the disclosure given above as well as the detailed description of the embodiment or embodiments given below, serve to explain the principles of this disclosure.

DETAILED DESCRIPTION

Figure 1:
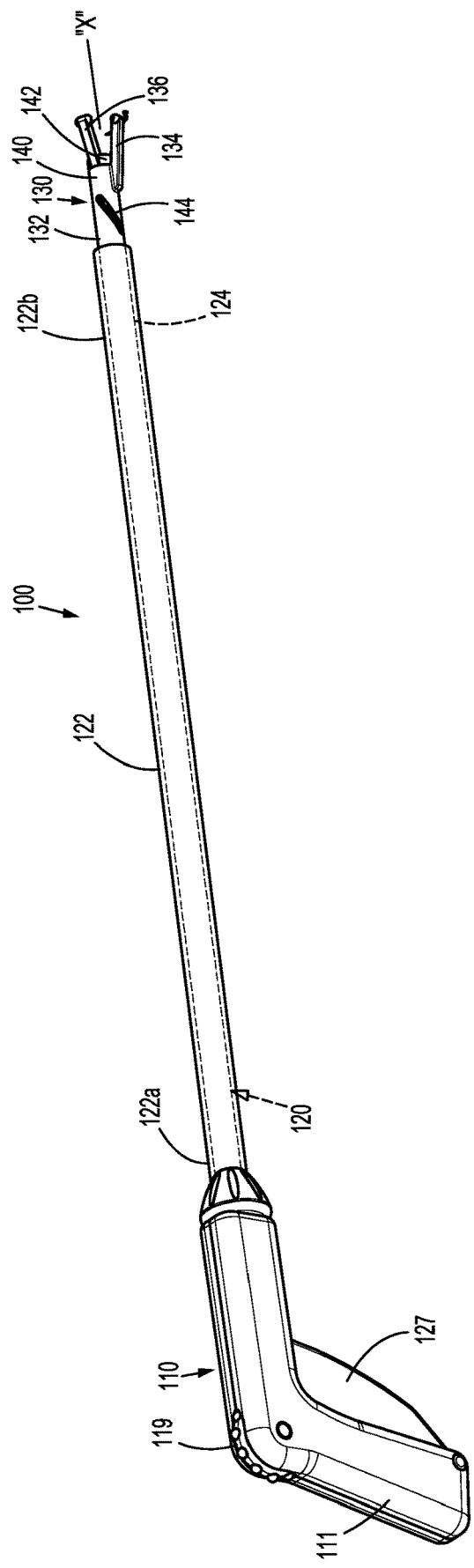
FIG. 1 is a perspective view of a surgical suturing instrument including a handle assembly, a shaft assembly, and an end effector assembly.

Various embodiments of the disclosed surgical suturing instruments for endoscopic, laparoscopic, endoluminal, and/or transluminal suturing will now be described in detail with reference to the drawings, wherein like reference numerals identify similar or identical elements. In the drawings and in the description that follows, the term "proximal" will refer to the portion of the surgical suturing instrument, or component thereof, that is closer to the user, while the term "distal" will refer to the portion of the surgical suturing instrument, or component thereof, that is farther from the user.

Performing suturing in an anal canal as well as other cylindrically shaped organs is a difficult and time-consuming task. It requires experience and skill to maneuverer the needle without hurting or damaging the neighboring, healthy tissue. Difficulty in purse string formation is one of the reasons that many surgeons do not elect to perform a TaTME surgery. Therefore, patients often miss out on the benefit of this procedure and are left with stomas.

As such, the disclosure provides a design enhancement in a side bite suturing device to facilitate the use of larger needles to get a bigger bite while suturing. The ends of a first jaw and a second jaw are split with a pivot point to allow for the jaws to hold larger needles. The instrument shaft is covered by an outer tube used to collapse the ends of both jaws into a trocar sized for insertion. Once the tip of the instrument is inside a peritoneal cavity, the outer tube may be slid proximally, relative to the jaws, to allow for a spring (e.g., a torsion spring) to open the ends of the jaws. The pivotable jaws allow for use of a suture having a diameter that is greater than a diameter of a typical trocar.

FIG. 1 illustrates a surgical suturing instrument 100 in accordance with an embodiment of the disclosure. The surgical suturing instrument 100 is configured to be particularly useful in endoscopic or laparoscopic procedures, wherein an end effector assembly 130 of the surgical suturing instrument 100 is insertable into a surgical site, via a trocar or the like. The surgical suturing instrument 100 includes a handle assembly 110, an inner shaft 120 extending distally from handle assembly 110, a slidable outer tube 122 disposed about the shaft 120, and the end effector assembly 130 coupled to the inner shaft 120.

The handle assembly 110 of the surgical suturing instrument 100 includes a handle housing 111 that supports a trigger 127 pivotably coupled to the handle housing 111. The trigger 127 is operably coupled to the end effector assembly 130 in a manner to rotate a first jaw member 134 of the end effector assembly 130 about a longitudinal axis "X" defined by the shaft 120 upon actuation of the trigger 127, as will be described in detail below.

Figure 2:
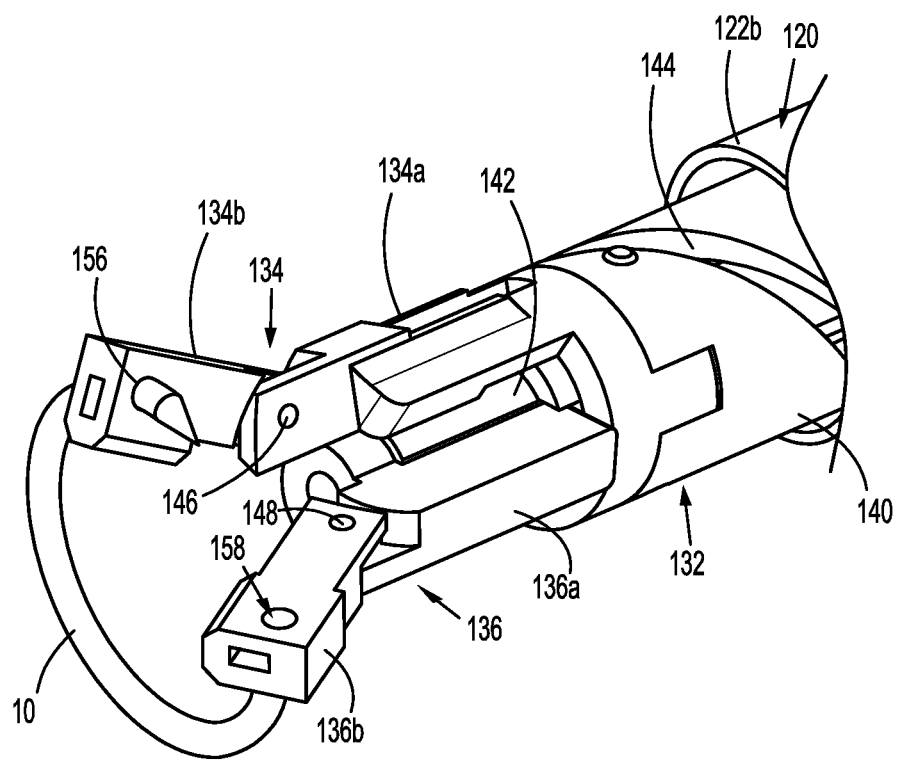
FIG. 2 is a partial perspective view of the end effector assembly of the surgical suturing instrument of FIG. 1.
Figure 3:
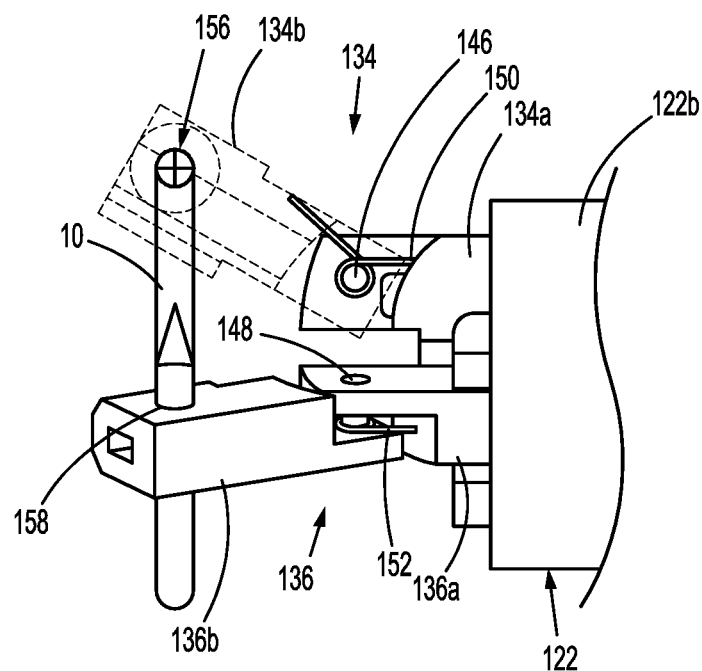
FIG. 3 is partial side view of the end effector assembly of FIG. 2 illustrating first and second jaw members thereof in an expanded state.

As shown in FIGS. 1-3, the end effector assembly 130 is coupled to a distal end portion 124 of the shaft 120 and generally includes an elongated body portion 132 and first and second jaw members 134, 136 each coupled to a distal end portion of the body portion 132. In some aspects, the jaw members 134, 136 may be pivotably coupled to the body portion 132. The body portion 132 has a proximal portion attached to the distal end portion 124 of the shaft 120. The end effector assembly 130 may be articulatable relative to the shaft 120. For example, the body portion 132 may be pivoted or articulated relative to the shaft 120 using a pair of cables (not shown) that extend from the handle assembly 110 and connect to opposite sides of the body portion 132. In use, it is contemplated that as one cable is pulled proximally, the other cable is drawn distally (or let out) to articulate the end effector assembly 130 relative to the shaft 120.

The body portion 132 of the end effector assembly 130 includes a rotatable outer shaft 140 and a fixed inner shaft 142 disposed at least partially within the outer shaft 140. The outer shaft 140 has the first jaw member 134 coupled to a distal end portion thereof, and the inner shaft 142 has the second jaw member 136 coupled to a distal end portion thereof such that the first jaw member 134 rotates with a rotation of the outer shaft 140 about the longitudinal axis "X," whereas the second jaw member 136 remains fixed. In some aspects, one or both of the jaw members 134, 136 may be configured to rotate about the longitudinal axis "X." The outer shaft 140 of the body portion 132 defines a helical cam slot 144 formed therein. In some embodiments, the cam slot 144 may assume a variety of patterns, for example, zig-zag, undulating, or the like.

The end effector assembly 130 includes an actuation bar (not explicitly shown) that is configured to translate along the longitudinal axis "X" in response to an actuation of the trigger 127 of the handle assembly 110. In particular, the actuation bar has a proximal end portion operably coupled to the trigger 127, and a distal end portion having a projection or boss slidably received within the cam slot 144 of the outer shaft 140. Upon an axial translation of the actuation bar relative to the body portion 132 of the end effector assembly 130, the boss of the actuation bar moves through the cam slot 144 of the outer shaft 140 to rotate the outer shaft 140 about the longitudinal axis "X" and, in turn, rotates the first jaw member 134 relative to the second jaw members 136.

The first and second jaw members 134, 136 each have a proximal end portion 134a, 136a, such as, for example, a fixed arm, and a distal end portion 134b, 136b, such as, for example, a pivoting arm. The pivoting arm or distal end portion 134b, 136b of each of the first and second jaw members 134, 136 is movably (e.g., pivotably) coupled to the respective fixed arm or proximal end portion 134a, 136a via a pivot pin 146, 148. The distal end portion 134b, 136b of each of the jaw members 134, 136 is configured to pivot between a collapsed or linearly-extending state (FIG. 4A) and an expanded or angled state (FIG. 4B) relative to the proximal end portion 134a, 136a. In aspects, the distal end portions 134b, 136b may be configured to slide relative to the proximal end portion 134a, 136a between the collapsed and expanded states. The proximal end portion 134a of the first jaw member 134 is coupled to the outer shaft 140 of the body portion 132, and the proximal end portion 136a of the second jaw member 136 is fixed to the inner shaft 142. In some embodiments, the proximal end portions 134a, 136a of the first and second jaw members 134, 136 may be pivotably connected to the body portion 132 via a joint, for example, a hinge or a knuckle/clevis.

Each of the jaw members 134, 136 includes a biasing member 150, 152 (FIG. 3), such as, for example, a pivot, leaf, or torsion spring attached to the pivot pin 146, 148 between the proximal and distal end portions 134a, 136a, 134b, 136b. The pivot springs 150, 152 resiliently bias the distal end portion 134b, 136b of each of the first and second jaw members 134, 136 outwardly (to the expanded or angled state) relative to the respective proximal end portion 134a, 136a.

The outer tube 122 of the surgical suturing instrument 100 is disposed about the shaft 120 and has a proximal end portion 122a coupled to a trigger 119 (FIG. 1), and a distal end portion 122b. The trigger 119 is configured to selectively retract and advance the outer tube 120 relative to the end effector assembly 130. The outer tube 122 is configured to move between a proximal position (FIGS. 2 and 4B), in which the distal end portion 122b of the outer tube 122 is disposed proximally of the distal end portion 134b, 136b of the first and second jaw members 134, 136, and a distal position (FIG. 4A), in which the distal end portion 122b of the outer tube 122 is disposed over the distal end portion 134b, 136b of the first and second jaw members 134, 136. When the outer tube 122 is in the distal position, the outer tube 122 maintains the first and second jaw members 134, 136 in a collapsed state, and when the outer tube 122 is in the distal position, the resilient bias of the biasing members 150, 152 is free to rotate the distal end portion 134b, 136b of the first and second jaw members 134, 136 outwardly (to the expanded or angled state) relative to the proximal end portion 134a, 136a of the respective jaw members 134, 136. While the outer tube 122 is described as being translatable, it is contemplated that the shaft 120 may also be translatable.

The distal end portion 134b, 136b of each of the first and second jaw members 134, 136 defines a hole or aperture 156, 158 therein sized and dimensioned for detachable and/or selective receipt of an end of a curved suture needle 10. The holes 156, 158 may extend entirely through a thickness of first and second jaw members 134, 136, respectively. In some embodiments, the holes 156, 158 may only extend partially through a thickness of first and second jaw members 134, 136. The holes 156, 158 are configured to selectively retain an end of curved needle 10 therein such that needle 10 may be passed to and from first and second jaw members 134, 136 during a surgical procedure. In particular, each of the holes 156, 158 may have disposed therein a touch latch or push latch (not explicitly shown) having pivotable engagement portions or hooks for selectively engaging and releasing opposing ends of curved needle 10. In addition, each opposing end of the curved needle 10 may have a hole or recess defined therein configured to selectively engage the push latch disposed in each of the holes 156, 158 of jaw members 134, 136.

The surgical suturing instrument 100 may include blades, wires, or thin cables (not shown) that extend through channels defined through first and second jaw members 134, 136. The wires are fabricated from an elastic, malleable material, for example, an elastomer, a shape memory alloy or a shape memory plastic. The wires are configured to move in opposite longitudinal directions through the channels defined through jaw members 134, 136 to selectively pass in and out of holes 156, 158 of first and second jaw members 134, 136. Distal ends of the wires are configured to interlock with an aperture or indentation (not shown) defined in opposite ends of curved needle 10 to prevent the curved needle 10 from detaching from the selected jaw member 134 or 136. In particular, as one wire moves into a hole 156 or 158 of its respective jaw member 134 or 136 and the corresponding aperture of the curved needle 10, the other wire moves out of the hole 156 or 158 of its respective jaw member 134 or 136 and the corresponding aperture of the curved needle 10. In this way, the curved needle 10 may be detachably retained within either of the first and second jaw members 134, 136 due to the engagement of a distal end of one of the wires or blades with an end of the curved needle 10.

Figure 4A:
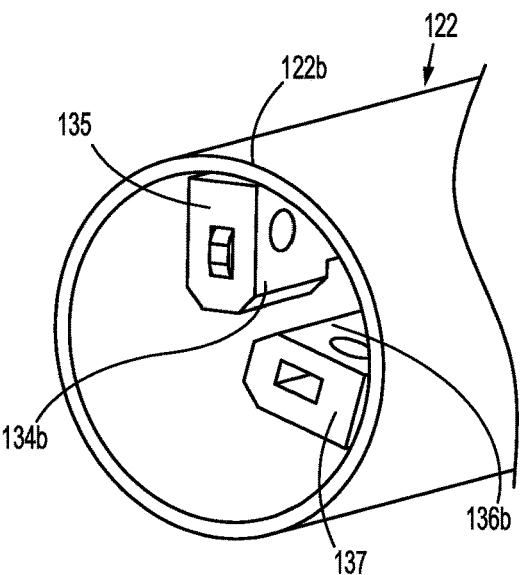
FIG. 4A is a partial perspective view of the end effector assembly of FIG. 2 illustrating an outer tube in a distal position and the first and second jaw members in a collapsed state.

In operation, to perform a minimally invasive procedure involving a suturing of tissue, an access tube or trocar is positioned through surface tissue or a natural opening in a patient to gain access to the surgical site within a body of the patient. As shown in FIG. 4A, the outer tube 122 of the surgical suturing instrument 100 is disposed in the distal position (relative to the shaft 120), whereby the distal end portion 122b of the outer tube 122 extends distally past the pivot pins 146, 148 (FIGS. 2 and 3) of the first and second jaw members 134, 136 to maintain the first and second jaw members 134, 136 in a collapsed state. In the collapsed state, a distal end 135, 137 of each of the first and second jaw members 134, 136 is coaxial with the proximal end portion 134a, 136a of the respective jaw members 134, 136, and the distal end portion 134b, 136b is disposed at an angle of about 0 degrees from the respective proximal end portion 134a, 136b of the respective jaw members 134, 136.

Figure 4B:
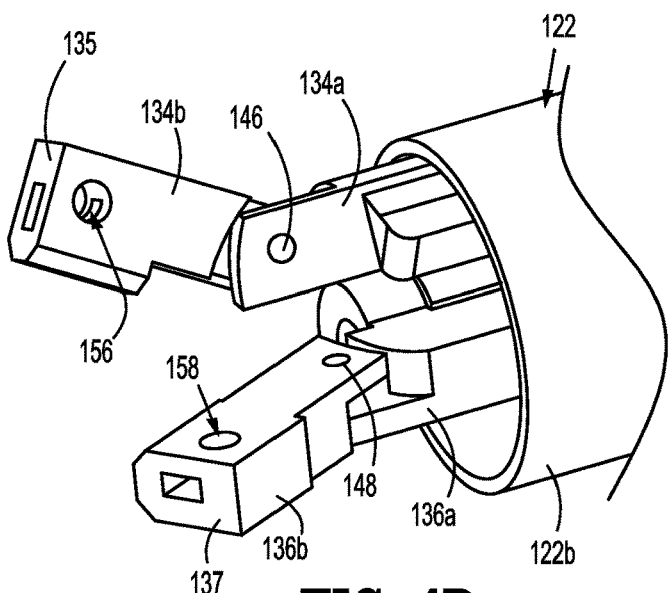
FIG. 4B is a partial perspective view of the end effector assembly of FIG. 2 illustrating the outer tube in a proximal position and the first and second jaw members in an expanded state.
Figure 4C:
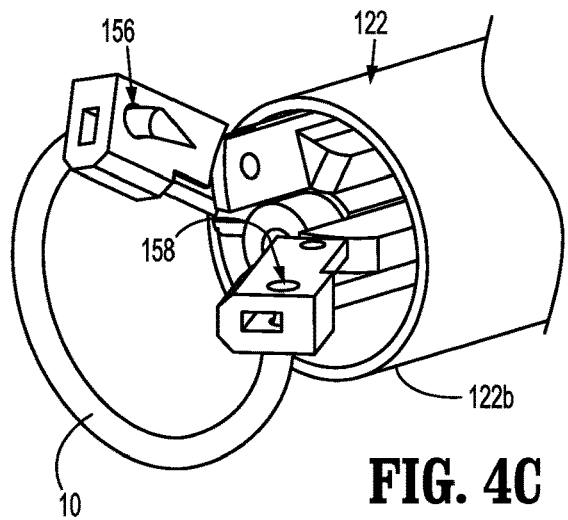
FIG. 4C is a partial perspective view of the end effector assembly of FIG. 2 illustrating a curved needle attached between the first and second jaw members.
Figure 5:
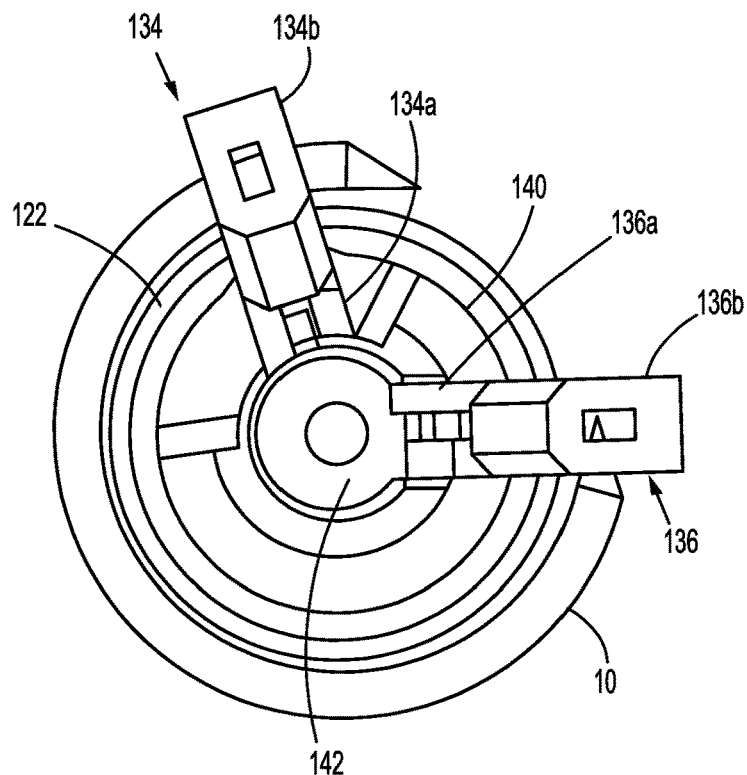
FIG. 5 is a front view illustrating the first and second jaw members of FIG. 3 in the expanded state.

With the outer tube 122 in the distal position, the jaw members 134, 136 assume a reduced outer profile, thereby allowing the surgical suturing instrument 100 to be passed through the cannula or trocar. The jaw members 134, 136, with curved needle 10, are passed through the trocar and positioned adjacent the subject tissue. It is contemplated that the curved needle 10 may be attached to the jaw members 134, 136 either before or after passing the jaw members 134, 136 through the trocar. Upon positioning the jaw members 134, 136 adjacent the subject tissue, the outer tube 122 and shaft 120 may be translated relative to one another to expose or deploy the jaw members 134, 136, as shown in FIG. 4B.

With the outer tube 122 no longer covering the distal end portion 134b, 136b of the jaw members 134, 136, the biasing members 150, 152 drive a rotation of the distal end portion 134b, 136b of each of the first and second jaw members 134, 136 outwardly to an expanded or angled state, such that the distal end portion 134b, 136b of each of the first and second jaw members 134, 136 is disposed at an angle from about 5 degrees to about 90 degrees relative to the proximal end portion 134a, 136b. In the expanded state, the distal end 135, 137 of each of the first and second jaw members 134, 136 is disposed outside of a respective longitudinal axis defined by the proximal end portions 134a, 136a of the jaw members 134, 136.

Because the jaw members 134, 136 are able to selectively assume a reduced overall outer profile, the jaw members 134, 136 may be larger than typical to accommodate larger than typical needles without having to utilize a larger diameter trocar/cannula.

In aspects, various end effector assemblies 130 may be provided with each having jaw members 134, 136 with distal end portions 134b, 136b configured to assume a discrete angle relative to the proximal end portion 134a, 136a in the expanded state. As such, each unique end effector assembly 130 is configured to accommodate a correspondingly sized curved needle. For example, a larger needle will require an end effector assembly 130 having jaw members 134, 136 with distal end portions 134b, 136b that pivot outwardly to a greater extent, whereas a smaller needle will require an end effector assembly 130 having jaw members 134, 136 with distal end portions 134b, 136b that pivot outwardly to a lesser extent.

The arcuate needle 10 may be fabricated from a shape memory material, such that the arcuate needle 10 is collapsible to a reduced profile to allow for passage through a trocar and expandable to a preset shape upon exiting the trocar. The arcuate needle 10 may be hinged to allow for the arcuate needle 10 to transition between an expanded state and a collapsed state.

Figure 6:
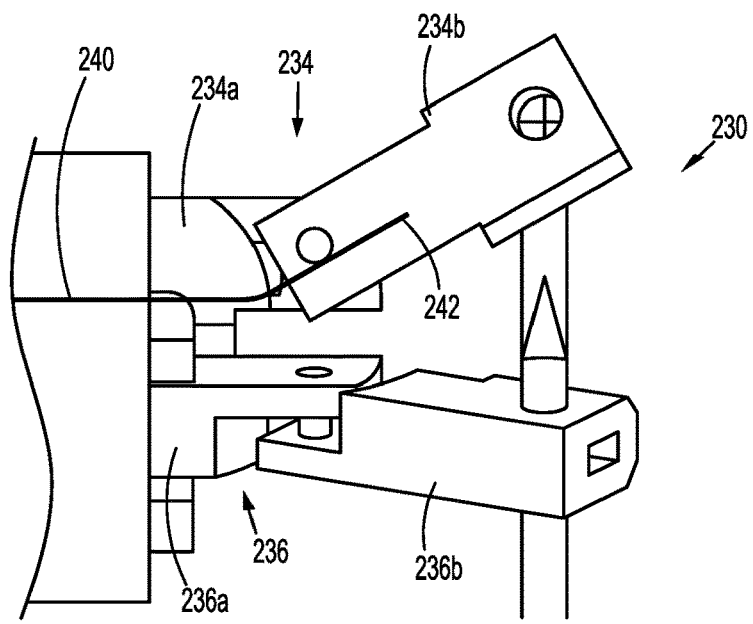
FIG. 6 is a partial side view of another embodiment of an end effector assembly illustrating a cable attached to one of the jaw members.

FIG. 6 illustrates another embodiment of an end effector assembly 230 of a surgical suturing instrument. The end effector assembly 230 is similar to the end effector assembly 130 described above with a difference being that jaw members 234, 236 of the end effector assembly 230 may be manually movable between a collapsed state and an expanded state. The end effector assembly 230 will only be described in the detail necessary to elucidate particular differences between the embodiments.

The end effector assembly 230 may be operable by a handle assembly, for example, the handle assembly 110 of FIG. 1, or any other suitable actuating mechanism. The first and second jaw members 234, 236 each have a proximal end portion 234a, 236a and a distal end portion 234b, 236b pivotably coupled to the respective proximal end portion 234a, 236a. A flexible cable 240 is provided that is axially translatable. The cable 240 has a proximal end portion (not shown) operably coupled to a separate trigger (not shown) of the handle assembly 110 (FIG. 1), and a distal end portion 242 fixed to a selected location of the distal end portion 234b of the first jaw member 234. The cable 240 is configured to pivot the distal end portion 234b of the first jaw member 234 relative to the proximal end portion 234a. The distal end portion 234b, 236b of the first and second jaw members 234, 236 may be resiliently biased to either the expanded or collapsed states. In aspects, a second cable (not shown) may be provided for selectively pivoting the distal end portion 236b of the second jaw member 236 relative to the proximal end portion 236a.

The surgical suturing instruments, or end effector assemblies thereof, described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the surgical suturing instruments, or component thereof, disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

It will be understood that various modifications may be made to the embodiments disclosed herein. Therefore, the above description should not be construed as limiting, but merely exemplifications of embodiments. Those skilled in the art will envision other modification within the scope and spirit of the claims appended thereto.

The invention claimed is:

1. A surgical suturing instrument, comprising:
   a handle assembly;
   a shaft extending distally from the handle assembly;
   a first jaw member including:
      a proximal end portion coupled to a distal end portion of the shaft;
      a distal end portion pivotably coupled to the proximal end portion of the first jaw member and configured for detachable connection of a curved needle; and
      a first biasing member that resiliently biases the distal end portion of the first jaw member radially outward relative to the proximal end portion to a preset angle; and
   a second jaw member including:
      a proximal end portion coupled to the distal end portion of the shaft;
      a distal end portion movably coupled to the proximal end portion and configured for detachable connection of the curved needle; and
      a second biasing member that resiliently biases the distal end portion of the second jaw member, radially outward relative to the proximal end portion of the second jaw member, to the preset angle.

2. The surgical suturing instrument according to claim 1, wherein the distal end portion of the second jaw member is pivotable relative to the proximal end portion between a first position, in which the distal end portion of the second jaw member is parallel with the proximal end portion, and a second position, in which the distal end portion of the second jaw member extends radially outward from the proximal end portion.

3. The surgical suturing instrument according to claim 1, further comprising an outer tube disposed about the shaft and configured to move between a proximal position, in which the outer tube is disposed proximally of the distal end portion of the second jaw member, and a distal position, in which the outer tube is disposed over the distal end portion of the second jaw member.

4. The surgical suturing instrument according to claim 3, wherein the second biasing member is configured to pivot the distal end portion of the second jaw member from a collapsed state to an expanded state relative to the proximal end portion in response to the outer tube moving from the distal position to the proximal position.

5. The surgical suturing instrument according to claim 1, further comprising an axially translatable cable having a distal end portion fixed to the distal end portion of the second jaw member, wherein the cable is configured to move the distal end portion of the second jaw member relative to the proximal end portion.

6. The surgical suturing instrument according to claim 1, wherein the proximal end portion and the distal end portion of the first jaw member are rotatable together about a central longitudinal axis defined by the shaft.

7. The surgical suturing instrument according to claim 6, wherein the proximal end portion of the second jaw member is fixed to the distal end portion of the shaft such that the second jaw member is prohibited from rotating relative to the shaft about the central longitudinal axis defined by the shaft.

8. The surgical suturing instrument according to claim 7, wherein the first and second jaw members each define a hole configured for detachable receipt of the curved needle, such that the first and second jaw members are configured to transfer the curved needle therebetween upon rotation of the first jaw member about the central longitudinal axis of the shaft relative to the second jaw member.

9. The surgical instrument according to claim 8, wherein the hole defined in each of the first and second jaw members is defined at least partially through the distal end portion of each of the first and second jaw members.

10. A surgical suturing instrument, comprising:
   a shaft defining a central longitudinal axis and having a distal end portion;
   an outer tube disposed about the shaft and configured to move axially relative to the shaft;
   a first jaw member including:
      a proximal end portion coupled to the distal end portion of the shaft; and
      a distal end portion pivotably coupled to the proximal end portion of the first jaw member and configured for detachable connection of a curved needle; and
      a first biasing member that resiliently biases the distal end portion of the first jaw member radially outward relative to the proximal end portion to a preset angle; and
   a second jaw member including:
      a proximal end portion coupled to the distal end portion of the shaft;
      a distal end portion pivotably coupled to the proximal end portion of the second jaw member and configured for detachable connection of the curved needle; and
      a second biasing member that resiliently biases the distal end portion of the second jaw member, radially outward relative to the proximal end portion of the second jaw member, to the preset angle, wherein the distal end portion of the first jaw member is configured to pivot relative to the proximal end portion of the first jaw member and the distal end portion of the second jaw member is configured to pivot relative to the proximal end portion of the second jaw member in response to axial movement of the outer tube relative to the shaft, wherein the proximal end portion and the distal end portion of the first jaw member are configured to rotate together about the central longitudinal axis of the shaft relative to the second jaw member.

11. The surgical suturing instrument according to claim 10, wherein the distal end portion of the first jaw member is pivotable relative to the proximal end portion of the first jaw member between a first position, in which the distal end portion of the first jaw member is coaxial with the proximal end portion of the first jaw member, and a second position, in which the distal end portion of the first jaw member is angled outward from the proximal end portion of the first jaw member.

12. The surgical suturing instrument according to claim 10, wherein the outer tube is configured to move between a proximal position, in which the outer tube is disposed proximally of the distal end portion of each of the first and second jaw members, and a distal position, in which the outer tube is disposed over the distal end portion of each of the first and second jaw members to maintain the first and second jaw members in a collapsed state.

13. An end effector assembly of a surgical suturing instrument, comprising:
   a body portion;
   a first jaw member including:
      a proximal end portion coupled to the body portion;
      a distal end portion pivotably coupled to the proximal end portion of the first jaw member and configured for detachable connection of a needle; and
      a first biasing member that resiliently biases the distal end portion of the first jaw member, radially outward relative to the proximal end portion to, a preset angle; and
   a second jaw member including:
      a proximal end portion coupled to the body portion;
      a distal end portion coupled to the proximal end portion and configured for detachable connection of the needle; and
      a second biasing member that resiliently biases the distal end portion of the second jaw member radially outward relative to the proximal end portion of the second jaw member to the preset angle, wherein the distal end portion of the second jaw member is configured to pivot relative to the proximal end portion between a first position, in which a longitudinal axis defined by the distal end portion is disposed at a first angle relative to the proximal end portion, and a second position in which the longitudinal axis of the distal end portion is disposed at the preset angle relative to the proximal end portion, the preset angle being greater than the first angle.

14. The end effector assembly according to claim 13, wherein the first angle is about zero degrees and the preset angle is from about 5 degrees to about 90 degrees.

15. The end effector assembly according to claim 13, wherein the distal end portion of the second jaw member has a distal end, the distal end being disposed coaxially with a longitudinal axis defined by the proximal end portion when the distal end portion of the second jaw member is in the first position, and the distal end being disposed outside of the longitudinal axis defined by the proximal end portion when the distal end portion of the second jaw member is in the second position.

* * * * *